United States Patent
Allegrini et al.

(10) Patent No.: US 7,605,268 B2
(45) Date of Patent: Oct. 20, 2009

(54) PROCESS FOR THE PREPARATION OF PYRIDINE COMPOUNDS

(75) Inventors: Pietro Allegrini, Milanese (IT); Marcello Rasparini, Pavia (IT); Gabriele Razzetti, Giovanni (IT); Roberto Rossi, Pavia (IT); Gianpiero Ventimigla, Cinisello Balsamo (IT)

(73) Assignee: Dipharma Francis s.r.l., Baranzate (IT)

( * ) Notice: Subject to any disclaimer, the term of this patent is extended or adjusted under 35 U.S.C. 154(b) by 55 days.

(21) Appl. No.: 11/737,852

(22) Filed: Apr. 20, 2007

(65) Prior Publication Data
US 2007/0249662 A1    Oct. 25, 2007

(30) Foreign Application Priority Data
Apr. 21, 2006  (IT) .......................... MI2006A0787
Oct. 11, 2006  (IT) .......................... MI2006A1949

(51) Int. Cl.
*C07D 401/12*    (2006.01)
(52) U.S. Cl. .................................. 546/273.7
(58) Field of Classification Search ............... 546/273.7
See application file for complete search history.

(56) References Cited

FOREIGN PATENT DOCUMENTS
ES    2 063 705 A1    1/1995

OTHER PUBLICATIONS

Ray et al., "Efficient Synthesis of, etc.," Synthetic Communications 37, 2861-2868, 2007.*
Radl et al., "Synthetic Studies connected, etc.," J of Heterocyclic Chemistry 43(6), 1447-1453, 2006.*

* cited by examiner

*Primary Examiner*—Patricia L Morris

(57) ABSTRACT

A process for preparation of a compound of formula (I), both as the isomeric mixture and individual isomers,

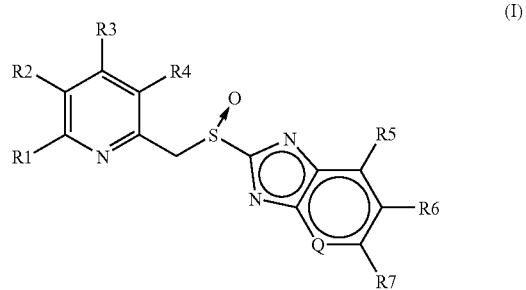

(I)

wherein Q is $=CR_8-$ or $=N-$; each $R_1$, $R_2$, $R_3$, $R_4$ is independently selected from hydrogen, halogen, hydroxy; nitro; $C_1$-$C_6$ alkyl optionally substituted with hydroxy; alkylthio $C_1$-$C_6$; $C_1$-$C_6$ alkoxy optionally substituted with halogen or $C_1$-$C_6$ alkoxy; phenyl-$C_1$-$C_6$ alkyl; phenyl-$C_1$-$C_6$ alkoxy; and —N(RaRb) wherein each Ra and Rb is independently hydrogen or $C_1$-$C_6$ alkyl or Ra and Rb, taken together with the nitrogen atom they are linked to, form a saturated heterocyclic ring; and each $R_5$, $R_6$, $R_7$, $R_8$ is independently selected from hydrogen, halogen, hydroxy; C1-C6 alkyl optionally substituted with hydroxy; alkylthio $C_1$-$C_6$; $C_1$-$C_6$ alkoxy optionally substituted with halogen; $C_1$-$C_6$ alkyl-carbonyl, $C_1$-$C_6$ alkoxy-carbonyl, and oxazol-2-yl; comprising converting a compound of formula (IV),

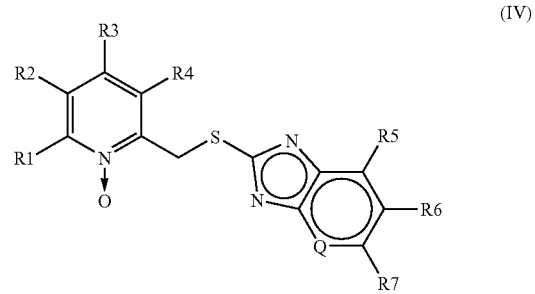

(IV)

to said compound of formula (I), in the presence of a catalyst, if necessary in an organic solvent.

1 Claim, No Drawings

PROCESS FOR THE PREPARATION OF PYRIDINE COMPOUNDS

FIELD OF THE INVENTION

The present invention relates to a novel process for the preparation of pyridine compounds useful in therapy, in particular in the treatment of pathologies related to an increase in gastric secretion.

TECHNOLOGICAL BACKGROUND

Sulfinyl compounds, which act as proton pump inhibitors, are used in the treatment of pathologies related to an increase in gastric secretion. Examples of these compounds, known as "prazoles", are omeprazole, esomeprazole, pantoprazole, rabeprazole, lansoprazole, tenatoprazole and hydroxymeprazole.

The synthesis of these products is substantially carried out following the scheme reported herein, in which $R_1$-$R_7$ and Q have, for example, the meanings defined in the disclosure.

It is evident that the process for their preparation requires many complex steps. Furthermore, a key step of the known processes is the oxidation of a thioether (—S—) intermediate to give the corresponding sulfinyl (—SO—) derivative. Hydrogen peroxide and sodium hypochlorite are usually preferred as oxidizing agents. The handling of large amounts of hydrogen peroxide involves, however, remarkable risks in term of safety of operators. Moreover, the oxidation of the thioether (—S—) intermediate, due to concomitant over-oxidation processes, can give undesired sulfone (—SO$_2$—) derivatives which have to be removed. This involves reduced yields and longer work up times. There is therefore the need for an alternative, advantageous process for the preparation of said compounds.

SUMMARY OF THE INVENTION

A novel process for the preparation of a pyridine compound of formula (I) has now been found, which overcomes the above mentioned technical problems and affords a pyri-

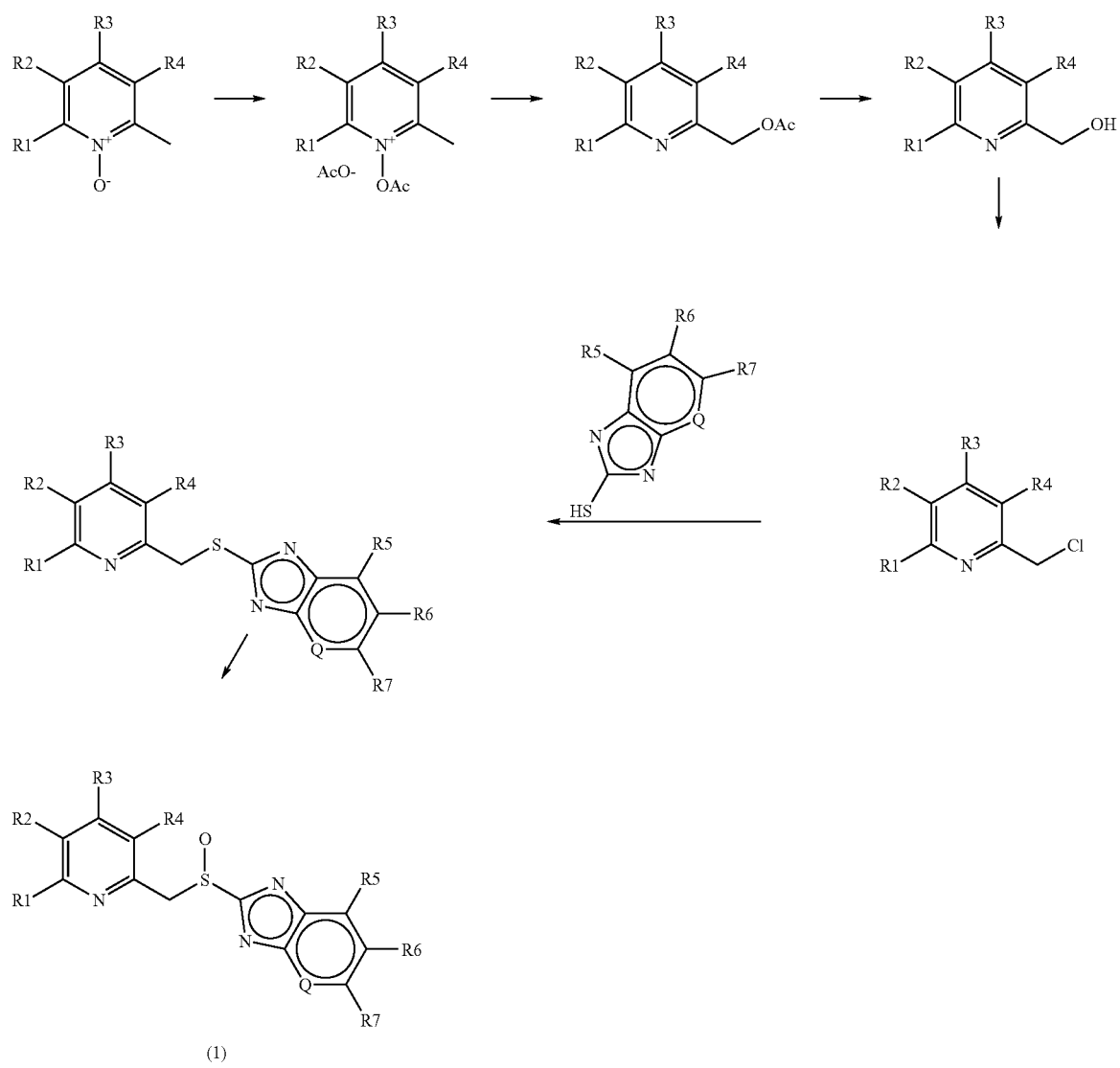

(1)

DETAILED DISCLOSURE OF THE INVENTION

The object of the invention is a process for the preparation of a compound of formula (I) or a salt thereof, both as the isomeric mixture and the individual isomer,

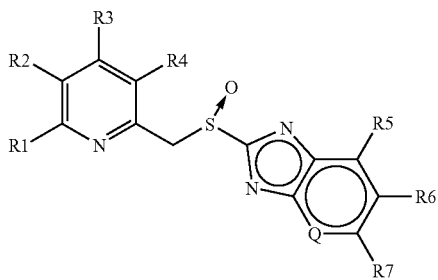

(I)

wherein

Q is =$CR_8$— or =N—;

each of $R_1$, $R_2$, $R_3$ and $R_4$ is independently selected from hydrogen, halogen, hydroxy; nitro; $C_1$-$C_6$ alkyl optionally substituted with hydroxy; $C_1$-$C_6$ alkylthio; $C_1$-$C_6$ alkoxy optionally substituted with halogen or $C_1$-$C_6$ alkoxy; phenyl-$C_1$-$C_6$ alkyl; phenyl-$C_1$-$C_6$ alkoxy; and —N(RaRb) wherein each Ra and Rb is independently hydrogen or $C_1$-$C_6$ alkyl or Ra and Rb, taken together with the nitrogen atom they are linked to, form a saturated heterocyclic ring; and each $R_5$, $R_6$, $R_7$ and $R_8$ is independently selected from hydrogen, halogen, hydroxy; $C_1$-$C_6$ alkyl optionally substituted with hydroxy; $C_1$-$C_6$ alkylthio; $C_1$-$C_6$ alkoxy optionally substituted with halogen; $C_1$-$C_6$ alkyl-carbonyl, $C_1$-$C_6$ alkoxy-carbonyl, and oxazol-2-yl; comprising converting a compound of formula (IV) or a salt thereof,

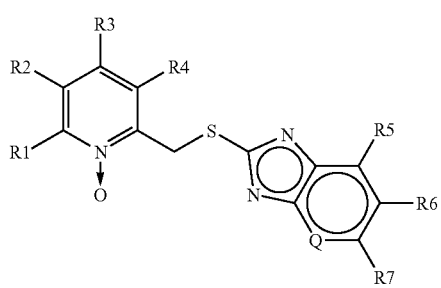

(IV)

wherein Q, $R_1$, $R_2$, $R_3$, $R_4$, $R_5$, $R_6$ and $R_7$ are as defined above, to said compound of formula (I), or salt thereof, in the presence of a catalyst, if necessary in an organic solvent, and, if desired, converting a compound of formula (I) to a salt thereof or to another compound of formula (I); and/or, if desired, resolving an isomeric mixture of a compound of formula (I) into the individual isomers.

A compound of formula (IV) can also be represented as follows

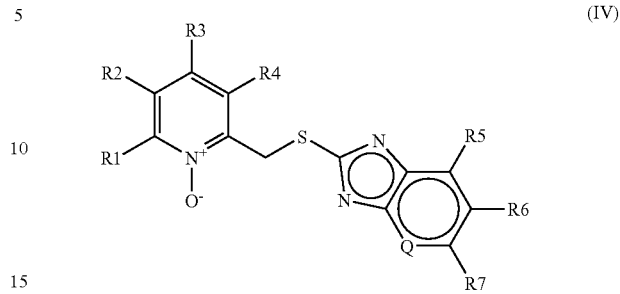

(IV)

wherein Q and $R_1$-$R_7$ are as defined above.

A salt of a compound of formula (I) or (IV) is preferably an acid or base addition salt, preferably a pharmaceutically acceptable salt.

An isomer of a compound of formula (I) can be, for example, a geometrical or optical isomer, preferably an (R)— or (S)— enantiomer.

An alkyl group in one of the above defined $R_1$-$R_8$ substituents, can be straight or branched, preferably is a $C_1$-$C_4$ alkyl group, in particular methyl, ethyl, propyl, isopropyl, butyl or tert-butyl, more preferably methyl, ethyl or propyl.

A halogen is fluorine, chlorine, bromine or iodine, preferably fluorine, chlorine or bromine.

A hydroxy substituted $C_1$-$C_6$ alkyl group is preferably a $C_1$-$C_4$ alkyl group substituted with one or two hydroxy groups, in particular —$CH_2OH$.

A $C_1$-$C_6$ alkoxy group substituted with halogen is preferably a $C_1$-$C_4$ alkoxy group substituted with one, two or three halogen, more preferably two or three fluorine, atoms, in particular —$OCHF_2$ or —$OCH_2CF_3$.

A $C_1$-$C_6$ alkoxy group substituted with $C_1$-$C_6$ alkoxy is preferably a $C_1$-$C_4$ alkoxy group substituted with $C_1$-$C_4$ alkoxy, in particular $C_1$-$C_3$ alkoxy —$OCH_3$.

A —N(RaRb) group is preferably an amino, methylamino, ethylamino, propylamino, dimethylamino group. When Ra and Rb, taken together with the nitrogen atom they are joined to, form a saturated heterocyclic ring, this can be a 5- or 6-membered heterocycle optionally containing a further nitrogen or oxygen atom. Examples of said group are pyrrolidino, piperidino, piperazino and morpholino.

Particularly preferred is a compound of formula (I), as defined above, wherein:

Q is =CH— or =N—;

$R_2$ is hydrogen, or $C_1$-$C_4$ alkyl optionally substituted with hydroxy;

$R_3$ is $C_1$-$C_4$ alkoxy optionally substituted with $C_1$-$C_4$ alkoxy or halogen;

$R_4$ is $C_1$-$C_4$ alkyl or $C_1$-$C_4$ alkoxy;

$R_6$ is hydrogen, $C_1$-$C_4$ alkoxy optionally substituted with halogen;

$R_7$ is hydrogen or $C_1$-$C_4$ alkoxy;

$R_1$ and $R_5$ are hydrogen;

or a salt thereof.

Specific examples of compounds of formula (I) are:

2-(3,4-dimethoxypyrid-2-yl)methanesulfinyl-5-difluoromethoxy-1H-benzimidazole(pantoprazole);

2-(4-chloro-3-methoxypyrid-2-yl)methanesulfinyl-5-difluoromethoxy-1H-benzimidazole;

5-methoxy-2-{[(4-methoxy-3,5-dimethyl-2-pyridinyl)methyl]sulfinyl}-1H-benzimidazole(omeprazole);

5-methoxy-2-{[(4-methoxy-3-methyl-5-hydroxymethyl-2-pyridinyl)-methyl]sulfinyl}-1H-benzimidazole(hydroxyomeprazole);

2-{[3-methyl-4-(2,2,2-trifluoroethoxy)-2-pyridinyl)methyl]sulfinyl}-1H-benzimidazole(lansoprazole);

2-{[3-methyl-4-(3-methoxy-propoxy)-2-pyridinyl)methyl]sulfinyl}-1H-benzimidazole(rabeprazole); and 5-methoxy-2-{[(4-methoxy-3,5-dimethyl-2-pyridinyl)methyl]sulfinyl}-1H-imidazo[4,5-b]pyridine(tenatoprazole);

and the salts thereof.

The conversion of a compound (IV) or a salt thereof to a compound (I) or a salt thereof, can be carried out at a temperature approx. ranging from −10° C. to the reflux temperature of the solvent or reaction mixture.

A catalyst is typically a metal catalysts having affinity for oxygen, based on a metal chosen from Ti(II), Ti(IV), V(II), V(III), V(V), Cr(II), Cr(III), Mn(III), Mn(IV), Fe(II), Fe(III), Nb(III), Mo(II), Mo(III), Mo(IV), Mo(V), W(II), W(III), W(IV), Tc(III), Re(III), Re(V), Ru(II), Ru(III), Ru(IV), Os(II), Os(III), Os(IV), Os(VI), Pd(II), Hf(IV), Pt(II) or Hg(II) or mixtures of two or more thereof, preferably mixtures of two thereof, and substituted by 1 to 8 ligands chosen from halides such as chloride or bromide, hydroxides, $C_1$-$C_6$ alkoxides, carboxylates (e.g. acetate or tartrate), carbonates, hydrogen carbonates, mineral acids salts (e.g. sulfate or phosphate), cyanides, cyanates, thiocyanates, dithiolates such as ethane-1,2-dithiolate, dialkylthiocarbamates such as diethyl dithiocarbamate, enolates such as acetylacetonate, phosphines (e.g. triphenylphosphine or tricyclohexylphosphine), chiral phosphines such as BINAP (2,2'-bis(diphenylphosphino)-1,1'-binaphthalene, cyclopentadienyl anions, carbon monoxide, olefins(ethylene and 1,4-cyclooctadiene), arenes (benzene), carbenes(benzylidene), heterocyclic carbenes (imidazolinidene) phthalocyanines, porphyrins(meso-tetraphenylporphyrin), amines such as triethylamine and piperidine, chelating amines such as ethylenediamine and aza-macrocycles such as 1,4,7,10-tetraazacyclododecane, heterocyclic ligands such as 1,10-phenanthroline, 8-hydroxy or 8-mercaptoquinoline or 2,2'-bipyridine, ethylenediamino tetraacetic acid and the salts thereof, nitriloacetic acid and the salts thereof, glyoximates (dimethyl glyoxime) and di-imine ligands, for example Salens ((R,R)—N,N'-Bis(3,5-di-tert-butylsalicylidene)-1,2-cyclohexanediamine), tartaric acid esters and amides.

A catalysts is preferably one as defined above, based on a metal chosen from V(II), V(III), V(V), Mo(II), Mo(III), Mo(IV), Mo(V), W(II), W(III), W(IV), Re(III), Re(V) and Ru(II), Ru(III), Ru(IV), or mixtures of two or more thereof, preferably mixtures of two thereof, and substituted by 1 to 8 ligands chosen from halides such as chloride and bromide, $C_1$-$C_4$ alkoxides, carbonates, ethylenediamino tetraacetic acid and the salts thereof for example with sodium, and di-imine ligands, for example Salens ((R,R)—N,N'-Bis(3,5-di-tert-butylsalicylidene)-1,2-cyclohexanediamine).

The catalyst can be prepared separately or in situ, according to known procedures.

The catalyst is typically present in amounts ranging from 0.5 to 20%, preferably from 1 to 10%, on the amount of compound (IV).

An organic solvent can be either a protic or aprotic solvent, typically an ether, e.g. tetrahydrofuran, dioxane, diethyl ether; a chlorinated solvent, e.g. dichloromethane, dichloroethane, tetrachloroethylene, chlorobenzene or dichlorobenzene; a $C_1$-$C_6$ alkanol, e.g. methanol, ethanol or isopropanol; an aliphatic or aromatic hydrocarbon, e.g. toluene; or an ester, e.g. ethyl acetate or butyl acetate; a dipolar aprotic solvent, e.g. acetonitrile, dimethylformamide, dimethylacetamide or dimethylsulfoxide; or a mixture of two or more of said solvents, particularly of 2 or 3 solvents.

The optional conversion of a compound (I) to another compound (I) or a salt thereof, as well as the resolution of an isomeric mixture of a compound (I) into the individual isomers, can be carried out with known methods.

A compound (IV) or a salt thereof can be prepared, for example, by reacting a compound of formula (II)

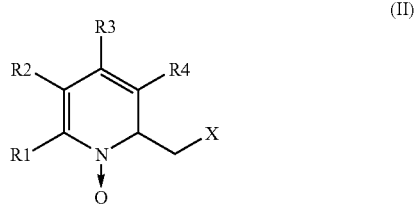

(II)

wherein $R_1$, $R_2$, $R_3$ and $R_4$ are as defined above, X is a leaving group; with a compound (III) or salts thereof,

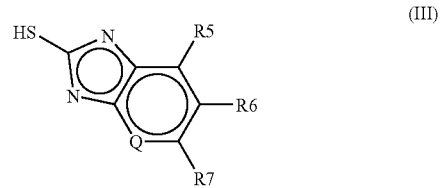

(III)

wherein Q, $R_5$, $R_6$ and $R_7$ are as defined above; in the presence of a basic agent and at room temperature, as reported in ES 2063705.

If desired the compound (IV) or a salt thereof, thus obtained, can be converted to a compound of formula (I) or a salt thereof, by the procedure of the present invention, without isolation from the reaction mixture.

If desired a compound (IV) or a salt thereof can be converted to another compound (IV) or a salt thereof, according to known methods, even without isolation form the reaction mixture.

The compounds of formula (II) and (III) and the salts thereof are known and can be prepared according to known methods, some of them being commercially available.

A salt of a compound of a compound of formula (II) or (III) is preferably an acid or base addition salt, preferably a pharmaceutically acceptable salt.

It has to be noticed that, according to ES 2063705, a compound (IV) can be converted to lansoprazole by reduction of the N-oxide group and subsequent oxidation of the thioether (—S—) intermediate to sulfoxide (—SO—), which however involves concomitant hyper-oxidation processes leading to undesired sulfonic (—$SO_2$—) derivatives.

The compounds of formula (IV), and the salts thereof, in which:

$R_3$ is —$O(CH_2)_3$—$OCH_3$, $R_4$ is $CH_3$, $R_1$, $R_2$ and $R_5$-$R_7$ are hydrogen and Q is =CH—; and $R_3$ and $R_4$ are $OCH_3$; $R_6$ is —$OCHF_2$, $R_1$, $R_2$, $R_5$ and $R_7$ are hydrogen and Q is =CH— are novel compounds and are a further object of the invention.

The process of the invention affords a pyridine derivative of formula (I) or a salt thereof, in a purity degree equal to or higher than 99.5%, typically higher than 99.9%, thereby fulfilling regulatory requirements. It is therefore evident that a The following examples illustrate the invention.

EXAMPLE 1

2-(4-Chloro-3-methoxypyrid-2-yl)methanesulfinyl-5-difluoromethoxy-1H-benzimidazole A 50 ml three-necked round-bottom flask equipped with magnetic stirring, reflux condenser and under nitrogen atmosphere, is loaded with $RuCl_3$ (63.1 mg, 0.30 mmol), THF (2.0 ml) and 1,4-dioxane (2.0 ml). After that, a solution of trisodium ETDA in water (0.13M, 2.37 ml, 0.30 mmol) is added, then a solution of 2-(4-chloro-3-methoxy-1-oxypyridin-2-ylmethylsulfanyl)-5-difluoromethoxy-1H-benzimidazole (1.178 g, 3.05 mmol) in 1,4-dioxane (12 ml) is dropped under reflux (about 80° C.). After 1 hr the mixture is cooled, the solvent is evaporated off under vacuum and the desired product is purified by flash chromatography.

$^1$H NMR (300 MHz, $CDCl_3$): δ 8.12 (1H, d, J=5.0 Hz), 7.54 (1H, d, J=8.7 Hz), 7.33 (1H, s), 7.25 (1H, d, J=5.0 Hz), 7.08 (1H, dd, J=8.7, 2.4 Hz), 6.52 (1H, t, J=74.1 Hz), 4.87 & 4.78 (2×1H, system AB, J=13.2 Hz), 3.85 (3H, s).

Following the same procedure, starting from the respective 1-oxypyridine derivatives, the following compounds can be obtained:

5-methoxy-2-{[(4-methoxy-3,5-dimethyl-2-pyridinyl) methyl]sulfinyl}-1H-benzimidazole;

5-methoxy-2-{[(4-methoxy-3-methyl-5-hydroxymethyl-2-pyridinyl)-methyl]sulfinyl}-1H-benzimidazole;

2-{[3-methyl-4-(2,2,2-trifluoroethoxy)-2-pyridinyl)methyl]sulfinyl}-1H-benzimidazole;

2-{[3-methyl-4-(3-methoxy-propoxy)-2-pyridinyl)methyl]sulfinyl}-1H-benzimidazole; and 5-methoxy-2-{[(4-methoxy-3,5-dimethyl-2-pyridinyl) methyl]sulfinyl}-1H-imidazo[4,5-b]pyridine.

EXAMPLE 2

2-(3,4-Dimethoxypyrid-2-yl)methanesulfinyl-5-difluoromethoxy-1H-benzimidazole(Pantoprazole)

A 25 ml three-necked round-bottom flask equipped with magnetic stirring, reflux condenser and under nitrogen atmosphere, is loaded with $RuCl_3$ (27.0 mg, 0.13 mmol), THF (1.0 ml), $H_2O$ (0.05 ml), trisodium ETDA hydrate (46.7 mg, 0.13 mmol). After that, a solution of 2-(3,4-dimethoxy-1-oxypyridin-2-ylmethylsulfanyl)-5-difluoromethoxy-1H-benzimidazole (500.0 mg, 1.30 mmol) in 1,4-dioxane (6 ml) is dropped and the mixture is heated to reflux (about 80° C.). After 1 hr the mixture is cooled, the solvent is evaporated off under vacuum and the desired product is purified by flash chromatography.

$^1$H NMR (300 MHz, d6-DMSO+NaOD) δ 8.23 (1H, d, J=5.4 Hz), 7.46 (1H. d, J=8.7 Hz), 7.26 (1H, d, J=4.8 Hz), 7.08 (1H, d, J=5.7 Hz), 7.03 (1H, t, JHF=84 Hz), 6.74 (1H, dd, J=5.7, 2.4 Hz), 4.63 & 4.38 (2×1H, system AB, J=12 Hz), 3.90 (3H, s), 3.78 (3H, s).

EXAMPLE 3

2-(4-Chloro-3-methoxypyrid-2-yl)methanesulfinyl-5-difluoromethoxy-1H-benzimidazole A 100 ml three-necked round-bottom flask equipped with magnetic stirring, reflux condenser and under nitrogen atmosphere, is loaded with 4-chloro-2-chloromethyl-3-methoxypyridine N-oxide (8.9 g, 43 mmol) 40 ml of THF, then a solution of 5-difluoromethoxy-2-mercapto-1H-benzimidazole (9.3 g, 43 mmol) and triethylamine (13 g, 128 mmol) in 20 ml of THF is added, keeping the temperature below 40° C. After 3 hrs, water is added (30 ml) to obtain a clear solution and 10% HCl is added to pH=5.

Trisodium ETDA monohydrate (1.54 g, 4.3 mmol) and $RuCl_3$ (0.9 g) are then added. The mixture is heated at 60° C. under nitrogen for 8 hrs, filtered through Celite and the solvent is evaporated off under vacuum. The residue is extracted with ethyl acetate and purified by flash chromatography thus obtaining the title compound.

Following the same procedure, the following compounds can be obtained:

5-methoxy-2-{[(4-methoxy-3,5-dimethyl-2-pyridinyl) methyl]sulfinyl}-1H-benzimidazole;

5-methoxy-2-{[(4-methoxy-3-methyl-5-hydroxymethyl-2-pyridinyl)-methyl]sulfinyl}-1H-benzimidazole;

2-{[3-methyl-4-(2,2,2-trifluoroethoxy)-2-pyridinyl)methyl]sulfinyl}-1H-benzimidazole;

2-{[3-methyl-4-(3-methoxy-propoxy)-2-pyridinyl)methyl]sulfinyl}-1H-benzimidazole; and 5-methoxy-2-{[(4-methoxy-3,5-dimethyl-2-pyridinyl) methyl]sulfinyl}-1H-imidazo[4,5-b]pyridine.

EXAMPLE 4

2-(4-(2,2,2-trifluoroethoxy)-3-methylpyrid-2-yl) methanesulfinyl-1H-benzimidazole(Lansoprazole)

A 25 ml three-necked round-bottom flask equipped with magnetic stirring, reflux condenser and under nitrogen atmosphere, is loaded with {Ru[(EDTA)H]Cl}Na.$H_2O$ (100 mg, 0.21 mmol), water (20 ml). The mixture is heated to 50° C. After that, a solution of 2-(4-(2,2,2-trifluoroethoxy)-3-methyl-1 oxypyrid-2-yl)methanesulfanyl-1H-benzimidazole (1.79 g, 4.84 mmol) in ethanol (50 ml) is added at the same temperature. After 1 hr stirring the mixture is cooled and the 2-(4-(2,2,2-trifluoroethoxy)-3-methylpyrid-2-yl)methanesulfinyl-1H-benzimidazole precipitates. The product is filtered and dried under vacuum. Yield: 50%.

$^1$H NMR (300 MHz, d6-DMSO) δ 8.29 (1H, d), 7.62 (2H. mbroad), 7.28 (2H, d), 7.07 (1H, d), 4.88 (2H, dd), 4.76 (2H, dd), 2.16 (3H, s).

EXAMPLE 5

2-{[3-Methyl-4-(3-methoxypropoxy)-2-pyridinyl) metyl]sulfanyl}-1H-benzimidazole(I) (Rabeprazole)

A 25 ml three-necked round-bottom flask equipped with magnetic stirring, reflux condenser and under nitrogen atmosphere, is loaded with 2-{[3-methyl-4-(3-methoxypropoxy)-1-oxy-2-pyridinyl)metyl]sulfanyl}-1H-benzimidazole (0.4 g 1.1 mmoles), acetonitrile (10 ml), Lithium carbonate (75 mg), $RuCl_3$ (18 mg, 0.1 mmoles) and $NaVO_3$ (15 mg, 0.12 mmoles). The mixture is heated to reflux 2 hours and analyzed by HPLC, showing a 5% of 2-{[3-Methyl-4-(3-methoxypropoxy)-2-pyridinyl)metyl]sulfinyl}-1H-benzimidazole.

EXAMPLE 6

5-methoxy-2-{[(4-methoxy-3,5-dimethyl-2-pyridinyl)methyl]sulfinyl}-1H-benzimidazole (omeprazole)

A 50 ml three-necked round-bottom flask equipped with magnetic stirring, reflux condenser and under nitrogen atmosphere, is loaded with RuCl(PPh$_3$)(SALEN) (SALEN=salycilaldehyde-ethylendiamine adduct) (0.77 mg, 0.0028 mmol), 5-methoxy-2-{[(4-methoxy-3,5-dimethyl-1-oxy-2-pyridinyl)methyl]sulfanyl}-1H-benzimidazole (100 mg, 0.289 mmol) and dichloromethane (3.0 ml). To the solution thus obtained a drop of iodobenzene and 0.5 mg of AgOAc are added and the solution is stirred overnight at reflux. The solvent is then evaporated and the residue is purified by flash chromatography affording 10 mg of omeprazole.

$^1$H NMR (300 MHz, CDCl$_3$): δ 8.24 (1H, s), 7.58 (1H, mbroad), 7.08 (1H, mbroad), 6.96 (1H, dd), 4.78&4.60 (2×1H, system AB,), 3.87 (3H, s), 3.72 (3H, s), 2.25 (3H, s), 2.23 (3H, s).

Following the same procedure, starting from the respective 1-oxypyridine derivatives, the following compounds can be obtained:

5-methoxy-2-{[(4-methoxy-3-methyl-5-hydroxymethyl-2-pyridinyl)-methyl]sulfinyl}-1H-benzimidazole;

2-(4-chloro-3-methoxypyrid-2-yl)methanesulfinyl-5-difluoromethoxy-1H-benzimidazole;

2-{[3-methyl-4-(2,2,2-trifluoroethoxy)-2-pyridinyl)methyl]sulfinyl}-1H-benzimidazole;

2-{[3-methyl-4-(3-methoxy-propoxy)-2-pyridinyl)methyl]sulfinyl}-1H-benzimidazole; and 5-methoxy-2-{[(4-methoxy-3,5-dimethyl-2-pyridinyl)methyl]sulfinyl}-1H-imidazo[4,5-b]pyridine.

The invention claimed is:

1. A compound of formula (IV), or a salt thereof,

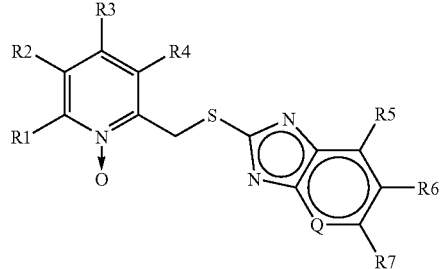

in which:

$R_3$ is —O—(CH$_2$)$_3$—OCH$_3$, $R_4$ is CH$_3$, Q is =CH—; and $R_1$, $R_2$ and $R_5$-$R_7$ are hydrogen; or $R_3$ and $R_4$ are OCH$_3$; $R_6$ is —OCHF$_2$, and Q is =CH—; and $R_1$, $R_2$, $R_5$ and $R_7$ are hydrogen.

* * * * *